United States Patent [19]

Procaccini et al.

[11] Patent Number: 4,734,434

[45] Date of Patent: Mar. 29, 1988

[54] METHOD FOR THE TREATMENT OF PRURITUS AND COMPOSITION FOR THE USE THEREIN

[75] Inventors: Robert L. Procaccini, Hatfield; Kim D. Lamon, Abington; Nicholas S. Hagen, Doylestown, all of Pa.

[73] Assignee: Rorer Pharmaceutical Corporation, Fort Washington, Pa.

[21] Appl. No.: 838,365

[22] Filed: Mar. 11, 1986

[51] Int. Cl.$^4$ .............................................. A61K 31/24
[52] U.S. Cl. ..................................... 514/535; 424/60; 424/157; 514/533; 514/887
[58] Field of Search ................. 424/60; 514/533, 535; 560/47

[56] References Cited

U.S. PATENT DOCUMENTS

| | | | |
|---|---|---|---|
| 3,692,818 | 9/1972 | Boltze et al. | 560/47 |
| 3,694,489 | 9/1972 | Boltze et al. | 560/47 |
| 3,767,811 | 10/1973 | Sherlock | 514/535 |

OTHER PUBLICATIONS

Chemical Abstracts 92:379e; 1980 (Jacobi et al).
Nakamura et al., Folia Pharmacol. Japan. 80, 183–194 (1982) (Eng. Translation).

*Primary Examiner*—Leonard Schenkman
*Attorney, Agent, or Firm*—James A. Nicholson; Alexis Barron; Martin F. Savitzky

[57] ABSTRACT

A method for the relief of pruritus comprising the administration of an effective antipruritic amount of a N-(trifluoromethylphenyl)anthranilic acid ester to an afflicted patient.

20 Claims, No Drawings

METHOD FOR THE TREATMENT OF PRURITUS AND COMPOSITION FOR THE USE THEREIN

FIELD OF THE INVENTION

This invention relates to a method for the treatment of dermatological disorders which are characterized by symptoms including pruritus.

Pruritis, or itch, can be an acute phenomenom or a chronic condition. It is a sensation which arises from the outermost fringes of the skin and leads to a purposive scratch reflex. The itch-scratch phenomenon involves a series of events including the stimulation of the cutaneous nociceptors, conduction by peripheral, afferent nerve fibers, central processing and interpretation and the scratch response. The scratch response, in itself, can aggravate the pruritus and result in skin abrasion, infection and continue a viscious and possibly destructive cycle.

REPORTED DEVELOPMENTS

Research into the causes of and treatment for pruritus has been limited and developments leading to antipruritic drugs have been, for the most part, a bonus of human clinical studies relating to the investigation of antiinflammatory drugs. These investigations have resulted in the discovery of the antipruritic effectiveness of certain potent antiinflammatory steroids such as fluocinide, betamethasone valerate, fluocinolone acetonide and triamcinolone acetonide. See, K. Kaidbey and A. Kligman, "Assay of Topical Corticosteroids: Efficacy of Suppression of Experimental Rhus Dermititis in Humans", Arch Dermatol, Vol 112, p 808–810(1976). However, it is well known that the use of such corticosteroids is associated with both cutaneous and systemic toxic side effects.

Local anesthetics have also been proposed as antipruritic agents, Dalili, H. and J. Adriani, "The Efficacy of Local Anesthetics in Blocking the Sensations of Itching, Burning, and Pain in Normal and 'Sunburned' Skin," *Clinical Pharmacology and Therapeutics*, 12: 913–919, 1971.

The present invention relates to the use of a nonsteroidal and nonanesthetic class of compounds for the treatment of conditions characterized by pruritic symptoms.

SUMMARY OF THE INVENTION

The present invention relates to a method for the relief of pruritus comprising the administration to a human or other mammal afflicted therewith an effective antipruritic amount of a N-(triflouromethylphenyl) anthranilic acid ester or a compound of Formula I:

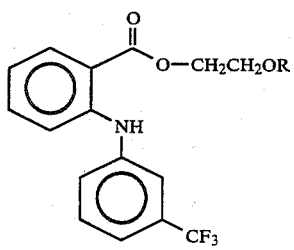

FORMULA I wherein: R is alkyl, hydroxy alkyl, acyloxy alkyl, alkoxy alkyl, or

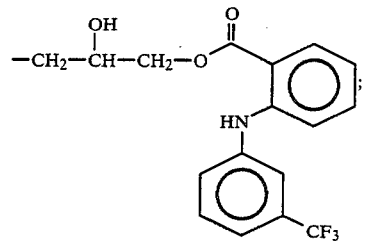

or a pharmaceutically acceptable salt thereof.

Another aspect of the present invention relates to a method for the prevention and/or treatment of ultraviolet ray-induced dermititis comprising the topical administration to the exposed skin of a human or other animal an effective amount of a compound of Formula I above.

A further aspect of this invention relates to a topical pharmaceutical composition comprising an effective antipruritic and/or ultraviolet ray absorbing amount of a compound according to Formula I, and a vehicle which is formulated to control the percutaneous absorption of a compound of Formula I.

The compounds described by Formula I are known and may be prepared in accordance with the method described in U.S. Pat. No. 3,692,818, hereby incorporated by reference.

DETAILED DESCRIPTION OF THE INVENTION

The term "pruritus" means itching which can range from a mild sensation to an intense sensation of itching pain.

The term "dermititis" means an inflammation of the skin, and includes dermatological conditions resulting from numerous causes such as allergic d., actinic d., contact dermititis, d. aestivalis, ambustionis d., d. articta, atopic d., berlock d., brown-tailed moth d., brucella d., d. bullosa, d. calorica, caterpillar d., d. congelationis, cosmetic d., cottonseed d., diaper d., d. epidemica, d. erythematosa, exfoliativa d., exfoliativa infantum, flannel moth d., fruit d., fungoid d., d. glandularis erythematosa, glue d., guayale d., halowax d., d. herpeetiformis, d. hiemalis, industrial d., insect d., d. medicamentosa, mycotic d., d. pediculoies ventricosus, primrose d., seborrheic d., d. solaris, tetryl d., d. venenata and weeping d., among others.

The term "alkyl" means an aliphatic hydrocarbon including about one to about eight carbon atoms in the chain which can be either straight or branched. The preferred alkyl groups are lower alkyl groups which include about one to about four carbon atoms.

The term "alkoxy" means an oxy radical including an aliphatic hydrocarbon group including about one to about eight carbon atoms in the chain which can be either straight or branched. The preferred alkoxy groups are lower alkoxy which include about one to about four carbon atoms.

The term "acyloxy" means an an alkyl substituted carboxyl radical. Preferred acyloxy groups include the lower alkyl substituted carboxyl groups.

The term "acyl" means an alkyl substituted carbonyl radical. Preferred acyl groups include lower alkanoyl groups.

The present invention may be used effectively for the relief of epidermal or dermal itching associated with any condition such as a systemic disease or allergy that affects epidermal and/or dermal nerve endings, an injury resulting in localized trauma affecting the epidermal or dermal nerve endings, or a localized dermititis.

A preferred method according to this invention comprises the relief of pruritic symptoms associated with a dermititis including actinic dermititis, contact dermititi such as an allergic dermititis or a contact dermititis caused by irritating substances of plant, animal, mineral or synthetic origin.

A special embodiment of the present invention comprises the treatment of pruritus associated with Rhus dermititis, such as the dermititis caused by contact with the genus of plants including poison ivy, poison oak and poison sumac.

The preferred class of compounds for use in the present invention are defined by Formula II below:

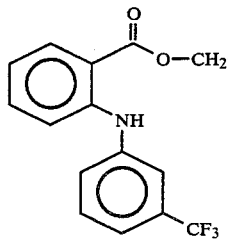

FORMULA II where $R_1$ is hydrogen, alkyl or acyl.

The most preferred compound for use in the method and composition of the present invention is where $R_1$ in Formula II is hydrogen and is also known by the tradename, etofenamate. The antiinflammatory, analgesic, erythema-blanching and inflammatory pain suppressive properties in animal studies of etofenamate has been reported by Nakamura et al, *Folia Pharmacol. Japon* 80, 183-194(1982). However, this report does not disclose that etofenamate possesses any antipruritic properties.

Another special embodiment comprises the use of the composition of the present invention for the prevention of ultraviolet ray-induced dermititis and the relief of the symptoms of such dermititis including the relief of pruritus and long term erythema.

The dosage regimen in carrying out the methods of the present invention is that which insures maximum therapeutic response until improvement is obtained and thereafter the minimum effective level which gives relief. Thus, in general, the dosages are those that are therapeutically effective in the treatment of pruritus and erythema associated with any particular dermititis. In general, in any specific case, consideration must be given to the patient's weight, general health, age, and other factors which may influence response to the drug. The daily dose regimen can range from about one to about four applications a day. It is believed that the composition of the present invention will be used most widely in applications which involve topical administration.

Compostitions useful in the practice of the present invention may be formulated for administration in any convenient way using one or more pharmaceutically acceptable carriers or excipients. The particular carrier and the ratio of active compound to carrier are determined by the solubility and chemical properties of the compounds, the particular mode of administration and standard pharmaceutical practice, and preferred compositions include about 0.1 to 10 wt % and most preferably about 3 to about 6 wt % of a compound of Formula I.

The present composition may also include other active ingredients, for example, $H_1$-antagonists, antibiotics, or local anesthetics.

Suitable carriers include diluents or fillers, sterile aqueous media and various non-toxic organic solvents. The compositions may be formulated in the form of powders, aqueous suspensions, or solutions, elixirs, syrups and contain one or more agents selected from the group including coloring agents and preserving agents, in order to provide a pharmaceutically acceptable preparation.

Aqueous suspensions can include an emulsifying or suspending agent. Diluents such as ethanol, propylene glycol, glycerin and their combinations can be employed as well as other materials. Additionally, gums, polymers or both can be added to the composition to act as film-formers or contribute to the waterproof coverup of the skin. Humectants and emollients may also be included to improve the feel of a topical composition. Dyes, pearlescents, insect repellants, water repellants, keratolytic agents, absorbants, and anti-caking agents may also be included. For a list of the commercially available ingredients, see McCutcheon's 1982 *Functional Ingredients*.

The compounds of Formula I are readily absorbed through the outermost layer of skin into the underlying structure thereof. Percutaneous absortion is observed, in particular, for the compounds of Fourmula I wherein R is hydroxy alkyl. The present topical composition is effective in prolonging the antipruritic action of the active ingredient by inhibiting the percutaneous absorption thereof and by preventing the premature diffusion of the active ingredient past the site of the pruritic sensation.

The preferred composition of this invention is formulated to provide for the delivery of the antipruritic compound at a suitable rate and concentration. The composition may be in the form of an aqueous suspension, an oil in water emulsion, a gel which can be a hydroalcoholic gel, a cream or an alcoholic solution. One method of providing for a vehicle which provides for a controlled percutaneous absorption of the active compound is to use a base which acts to inhibit the transfer of the active compound from the environment of the vehicle to the surface of the skin. The most preferred vehicle for a long-lasting antipruritic composition is preferably biphasic and may be a cream or oil in water emulsion. The biphasic vehicle includes an aqueous phase which comes in contact with the skin and a second nonaqueous phase which includes the bulk of the antipruritic agent.

Another method for controlling the percutaneous absorption of the active compound comprises the use of a percutaneous absorption control agent. The percutaneous absorption control agent possesses the characteristic of reversibly binding to the active ingredient in the vehicle and on the surface of the skin. The binding strength of the absorption agent is determined by the intended use of the composition. A stronger binding agent would be desirable when the composition is intended for use as an ultraviolet ray absorbing film, and a relatively weak binding strength is desirable for a fast acting but short term antipruritic composition. Exemplary absorption control agents include aluminum hydroxide gel or any other compound which is not readily absorbed through the skin and which possesses an affinity for ether linkages and hydroxyl groups. Aluminum hydroxide gel is the preferred control ingredient for compositions including compounds of Formula I wherein R is hydroxy alkyl. The control agent is included in the composition in an amount which is effective for retarding the percutaneous absorption of a compound of Formula I, and may be from about 0.001 to about 0.5 wt % based on the total weight of the composition, the preferred amount being from about 0.01 to about 1 wt %.

It will be observed that exemplary compositions according to this aspect of the present invention will possess antipruritic effectiveness for about one to about eight hours and exemplary preferred composition will possess anti-pruritic effectiveness for about three to about eight hours.

The present composition is also useful in the practice of the method for the prevention of ultraviolet ray induced dermititis. The application of the present composition to the exposed normal, healthy skin of the user can effectively shield the skin from the burning rays of the sun. The preferred composition, for this purpose, includes the maximum effective amount of percutaneous absorption inhibitor to reduce loss of effectiveness over time due to precutaneous absorption of the active compound of Formula I. The amount of compound of Formula I in such a composition comprises an amount sufficient to absorb from about 10 to about 100% of the burning rays of the sun, and is preferably about 1 to about 15 wt %.

An advantage of the present composition relates to its convenience in use. The composition may be used to prevent the damage caused by the burning rays of the sun and may be used also to alleviate the erythema and pruritus resulting from undue solar exposure.

Topical application of exemplary compositions within the scope of the present invention promptly alleviates the itch associated with the dermititi mentioned above. In particular, The relief of pruritic symptoms associated with Rhus dermititis occurs within a very short period of time, on the order of about 30 seconds or less after application of a gel composition including the antipruritic compound of Formula I. The gel composition is effective for about one to about four hours and application of the composition every few hours, about once every two to four hours is preferred. The cream formulation of the present composition and the composition including the percutaneous absorption control agent possess longer periods of effectivenesss and do not require a dosage regimen as frequent as the gel formulation to achieve the desired anti-pruritic effect.

The following formulations are examples of the composition according to the present invention and are not to be considered limiting thereof.

EXAMPLE I

The composition of this example is in the form of a gel and is prepared by mixing the following components labeled A. through D., the amounts of which are expressed as wt %.

| | | |
|---|---|---|
| A. | Deionized Water | 64.95 |
| | Carbomer 940 | 1.00 |
| | Preservative | 0.10 |
| B. | Deionized Water | 8.00 |
| | Sodium EDTA Solution | 0.10 |
| | Triethanolamine (99%) | 0.80 |

| | | |
|---|---|---|
| | -continued | |
| | Benzophenone - 4 | 0.05 |
| C. | Ethohexadiol | 5.00 |
| | Etofenamate | 5.00 |
| D. | Propylene Glycol | 13.00 |
| | PEG-7 Glyceryl Cocoate | 1.00 |
| | Aluminum Hydroxide Gel | 1.00 |

EXAMPLE II

This example is in the form of a glycol solution and is prepared by mixing the following components, the amounts of which are expressed in wt %.

| | | |
|---|---|---|
| A. | Ethohexadiol | 3.50 |
| | Etofenamate | 5.00 |
| B. | Propylene Glycol | 80.25 |
| | Aluminum Hydroxide | 1.00 |
| | PEG 200 | 10.00 |
| | $C_{12}$—$C_{15}$ Benzoate | 0.25 |

EXAMPLE III

This example is in the form of a cream which is prepared by mixing the following components, the amounts of which are expressed in wt %.

| | | |
|---|---|---|
| A. | Isopropyl Linoleate | 4.50 |
| | Wheat germ Glycerides | 0.25 |
| | BHA | 0.10 |
| B. | Dioctyl Maleate | 1.00 |
| | Preservative | 0.20 |
| | Cetearyl Alcohol (&) Ceteareth-20 | 6.00 |
| | Glyeryl Stearate | 7.50 |
| | Sorbitan Stearate | 1.00 |
| | Cetyl Alcohol | 3.00 |
| C. | Polypropylene Glycol Stearyl Ether | 3.00 |
| | Etofenamate | 5.00 |
| D. | Deionized Water | 68.30 |
| | Tetrasodium EDTA | 0.05 |
| | Preservative | 0.10 |

EXAMPLE IV

This example is in the form of a cream which is prepared by mixing the following components, the amounts of which are expressed in wt %.

| | | |
|---|---|---|
| A. | Mineral Oil (&) Lanolin Alcohol | 7.00 |
| | Polysorbate 60 | 3.50 |
| | Sorbitan Stearate | 1.50 |
| | PEG - 40 Stearate | 1.00 |
| | Glyceryl Stearate | 6.00 |
| | Cetyl Alcohol | 3.50 |
| B. | Ethohexadiol | 2.00 |
| | Etofenamate | 1.00 |
| C. | Deionized Water | 67.75 |
| | Aluminum Hydroxide | 0.50 |
| | Propylene Glycol | 6.00 |
| | Preservative | 0.25 |

EXAMPLE V

This example is in the form of a lotion which is prepared by mixing the following components, the amounts of which are expressed in wt %.

| | |
|---|---|
| Mineral Oil (&) Lanolin Alcohol | 2.50 |
| Polysorbate 60 | 1.25 |
| Sorbitan Stearate | 0.70 |

| | |
|---|---|
| PEG-40 Stearate | 0.50 |
| Glyceryl Stearate | 2.75 |
| Cetyl Alcohol | 0.75 |
| Ethohexadiol | 3.00 |
| Polypropylene Glycol Stearyl Ether | 3.00 |
| Etofenamate | 2.50 |
| Aluminum Hydroxide | 1.00 |
| Deionized Water | 79.30 |
| Propylene Glycol | 2.50 |
| Preservative | 0.25 |

EXAMPLE VI

This example is in the form of a hydrophilic ointment which is prepared by mixing the following components, the amounts of which are expressed in wt %.

| | |
|---|---|
| Isopropyl Linoleate | 4.00 |
| Wheat Germ Glycerides | 0.50 |
| BHT | 0.10 |
| Dioctyl Maleate | 2.00 |
| Preservative | 0.20 |
| Cetearyl Alcohol (&) Ceteareth-20 | 6.00 |
| Glyceryl Stearate | 8.00 |
| Sorbitan Stearate | 1.00 |
| Cetyl Alcohol | 2.00 |
| Polypropylene Glycol Stearyl Ether | 15.00 |
| Etofenamate | 10.00 |
| Deionized Water | 50.90 |
| Aluminum Hydroxide | 0.10 |
| Tetrasodium EDTA | 0.10 |
| Preservative | 0.10 |

EXAMPLE VII

This example is in the form of a spray solution which is prepared by mixing the following components, the amounts of which are expressed in wt %.

| | |
|---|---|
| Polypropylene Glycol Stearyl Ether | 1.50 |
| Ethohexadiol | 1.50 |
| Etofenamate | 4.00 |
| Ethyl Alcohol | 8.00 |
| Propylene Glycol | 84.90 |
| Aluminum Hydroxide | 0.10 |

EXAMPLE VIII

This example is in the form of an anionic cream which is prepared by mixing the following components, the amounts of which are expressed in wt %.

| | |
|---|---|
| Cholesterol-Sterol Liquid DF (Amerchol L-101) | 5.0 |
| Polysorbate 60, NF | 3.0 |
| Sorbitan monostearate, NF (Aralacel 60) | 2.0 |
| Polyoxyl 40 Stearate, NF (Myrj 52S) | 1.0 |
| Cetyl Alcohol (NF Flakes) | 2.5 |
| Glyceryl Stearate SE, DF (Cerasynt Q) | 7.0 |
| 2-Ethylhexane-1,3-diol | 4.0 |
| Etofenamate | 5.0 |
| Purified Water, USP | 59.0 |
| 5-Chloro-2-methyl-4-isothiazolin-3-one (Kathon CG) | 0.05 |
| Propylene Glycol, USP | 8.0 |
| Buffer Solution (21 wt % sodium citrate, 14 wt % citric acid, 12 wt % glycine in purified water) | 3.5 |

EXAMPLE IX

This example is in the form of a cream which is prepared by mixing the following components, the amounts of which are expressed in wt %.

| | |
|---|---|
| Ceraphyl IPL | 3.5 |
| Wichenol 535 (Wheat Germ Glycerides, Vita-Cos) | 0.25 |
| Antioxidant G-16 | 0.15 |
| Bernel Ester (Dioctyl Maleate) | 0.9 |
| Emercide 1199 (Phenoxyethanol & Chloroxylenol) | 0.2 |
| Promulgen D | 4.7 |
| Aralacel 165 | 8.4 |
| Aralacel 60 | 1.4 |
| Cetyl Alcohol (NF Flakes) | 1.1 |
| Arlamol E | 3.5 |
| Etofenamate | 5.0 |
| Purified Water | 60.0 |
| Hampene 100 Solution (Tetra sodium EDTA Solution) | 1.0 |
| Buffer Solution (21 wt % sodium citrate, 14 wt % citric acid, 12 wt % glycine in purified water) | 3.0 |
| Kathon CG | 0.05 |

Other compositions within the scope of the present invention may be prepared according to the present disclosure by any person ordinarily skilled in the art.

We claim:

1. A method for the relief of pruritus in a human or other mammal comprising administering to a human or other mammal afflicted therewith a topical composition comprising an effective percutaneous absorption inhibiting amount of aluminum hydroxide and an effective antipruritic amount of a compound of the formula:

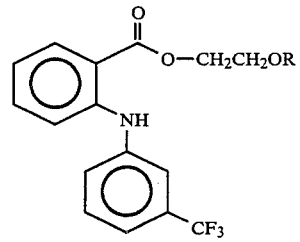

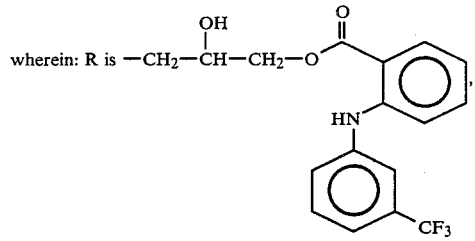

wherein: R is $-CH_2-CH(OH)-CH_2-O$ alkyl, hydroxy alkyl, acyloxy alkyl or alkoxy alkyl; or a pharmaceutically acceptable salt thereof.

2. A method according to claim 1, wherein said pruritus is associated with a dermititis.

3. A method according to claim 2, wherein said dermititis is an allergic dermititis, actinic dermititis, or a contact dermititis caused by an irritating substance derived from plant, animal or synthetic origin.

4. A method according to claim 3, wherein said dermititis is a contact dermititis.

5. A method according to claim 4, wherein said contact dermititis is a Rhus dermititis.

6. A method for the relief of the itching, redness and inflammation associated with contact dermititis or actinic dermititis comprising the topical administration to the skin of a human or other mammal afflicted therewith, a composition comprising percutaneous absorption inhibiting amount of aluminum hydroxide, and a topically effective amount of a compound of the formula

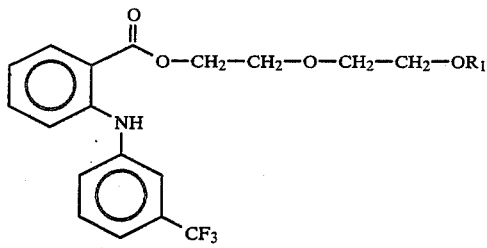

wherein $R_1$ is hydrogen, acetyl or lower alkyl.

7. A method according to claim 6, wherein said dermititis is a Rhus dermititis.

8. A method according to claim 6, comprising the topical administration of an effective anti-itching amount of etofenomate.

9. A method according to claim 6, wherein said Rhus dermititis is caused by contact with poison ivy, poison oak or poison sumac.

10. A method according to claim 6, wherein said composition is administered topically from about one to about four times a day.

11. A method for the relief of a chronic or acute epidermal pruritic sensation comprising the topical administration to a human or other mammal's skin in which said pruritic sensation is localized, a composition including about 0.01 to about 1 wt% of aluminum hydroxide and a topically effective amount of etofenamate.

12. A method for the prevention of sunburn in humans or other mammals comprising the topical administration to the normal, healthy exposed skin thereof of an effective ultraviolet ray absorbing amount of a compound of the formula

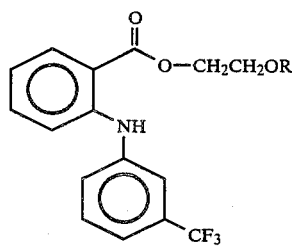

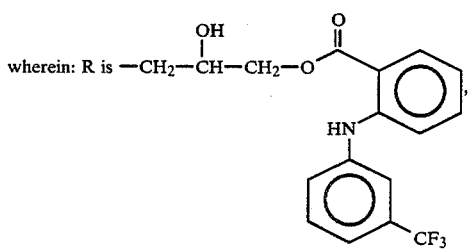

alkyl, hydroxy alkyl, acyloxy alkyl or alkoxy alkyl; or a pharmaceutically acceptable salt thereof.

13. A method according to claim 12 comprising (1) applying topically an effective ultraviolet ray-absorbing amount of said compound to said normal, healthy exposed skin thereby forming a film of said compound on the surface of said skin, and (2) exposing said skin to the rays of the sun.

14. A method according to claim 13 wherein said normal, healthy exposed skin shows no visible signs of inflammation or erythema.

15. A method according to claim 14 wherein said compound is etofenamate and is topically applied to the skin in the form of a composition comprising about one to about 15 wt % of etofenamate and a percutaneous absorption inhibitor.

16. A method according to claim 15 wherein said percutaneous absorption inhibitor comprises about 0.01 to about 1 wt % of aluminum hydroxide.

17. An anti-pruritic composition comprising an effective anti-pruritic amount of etofenamate in a pharmaceutically acceptable vehicle formulated to inhibit the percutaneous diffusion of said etofenamate and including aluminum hydroxide.

18. An anti-pruritic composition according to claim 17, comprising from about 0.001 to about 0.5 wt % of aluminum hydroxide.

19. A method for the long-term relief of ultraviolet ray-induced erythema in humans comprising topically administering to a human or other mammal afflicted therewith a composition comprising an effective percutaneous absorption inhibiting amount of aluminum hydroxide and an effective blanching amount of a compound of the formula:

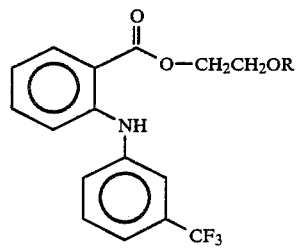

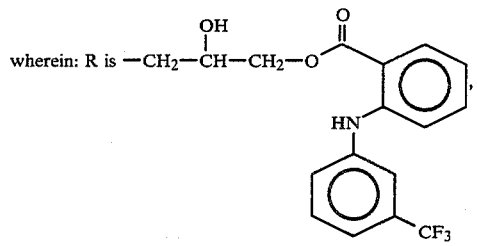

, alkyl, hydroxy alkyl, acyloxy alkyl or alkoxy alkyl; or a pharmaceutically acceptable salt thereof.

20. A method for the deterrence of skin damage caused by the undue exposure of human skin to the ultraviolet rays of the sun comprising:

(1) applying topically to exposed human skin showing no visible signs of inflammation or erythema a composition including about one to about 15 wt% of etofenamate and about 0.1 to about 1 wt % of aluminum hydroxide thereby forming on the surface of said skin an effective ultraviolet ray-absorbing film; and (2) exposing said skin to the ultraviolet rays of the sun.

* * * * *